United States Patent
Everett et al.

(10) Patent No.: US 7,293,308 B2
(45) Date of Patent: Nov. 13, 2007

(54) METHOD AND APPARATUS FOR AUTOMATIC SELF-ALIGNING DOCKING OF A COUCH WITH A MAGNETIC RESONANCE IMAGING SCANNER

(75) Inventors: Dennis K. Everett, Seven Hills, OH (US); Timothy Bielawski, Maple Heights, OH (US); Patrick T. Cumpson, Chesterland, OH (US)

(73) Assignee: Koninklijke Philips Electronics N. V., Eindhoven (NL)

( * ) Notice: Subject to any disclaimer, the term of this patent is extended or adjusted under 35 U.S.C. 154(b) by 259 days.

(21) Appl. No.: 10/536,466

(22) PCT Filed: Nov. 19, 2003

(86) PCT No.: PCT/IB03/05305

§ 371 (c)(1),
(2), (4) Date: May 25, 2005

(87) PCT Pub. No.: WO2004/047639

PCT Pub. Date: Jun. 10, 2004

(65) Prior Publication Data

US 2006/0167356 A1    Jul. 27, 2006

Related U.S. Application Data

(60) Provisional application No. 60/429,703, filed on Nov. 27, 2002.

(51) Int. Cl.
*A61B 6/04* (2006.01)
(52) U.S. Cl. .............................. 5/601; 5/600; 378/209; 378/20

(58) Field of Classification Search .................... 5/601, 5/600; 378/209, 20, 204, 205, 208; 600/415
See application file for complete search history.

(56) References Cited

U.S. PATENT DOCUMENTS

| 4,131,802 | A | * | 12/1978 | Braden et al. | 378/20 |
| 4,567,894 | A | | 2/1986 | Bergman | 128/653 |
| 4,638,252 | A | * | 1/1987 | Bradshaw | 324/318 |
| 4,671,728 | A | | 6/1987 | Clark et al. | 414/401 |
| 4,727,328 | A | * | 2/1988 | Carper et al. | 324/318 |
| 4,914,682 | A | * | 4/1990 | Blumenthal | 378/20 |
| 5,448,607 | A | * | 9/1995 | McKenna | 378/4 |
| 5,499,415 | A | * | 3/1996 | McKenna | 5/601 |
| 5,525,905 | A | * | 6/1996 | Mohapatra et al. | 324/318 |

(Continued)

FOREIGN PATENT DOCUMENTS

| EP | 1 004 269 | 5/2000 |
| JP | 2000-232969 | 8/2000 |

*Primary Examiner*—Robert G. Santos (57) ABSTRACT

A docking assembly connected to a movable couch (30) docks the couch with an imaging apparatus (10). Couch alignment surfaces (72) mate with corresponding alignment surfaces (64) of a connecting region (50) of the imaging apparatus (10) to define a docked position of the movable couch (30) with respect to the imaging apparatus. A docking sensor (160) detects the movable couch (30) approaching the docked position. A latch (82) mates with the connecting region (50) of the imaging to apparatus (10). An actuator (130, 154) cooperates with the latch (82) to bias the movable couch (30) into the docked position responsive to a signal produced by the docking sensor (160).

23 Claims, 9 Drawing Sheets

U.S. PATENT DOCUMENTS

| | | | |
|---|---|---|---|
| 5,638,419 A * | 6/1997 | Ingwersen | 378/4 |
| RE36,415 E * | 11/1999 | McKenna | 378/4 |
| 6,003,174 A * | 12/1999 | Kantrowitz et al. | 5/601 |
| 6,199,233 B1 * | 3/2001 | Kantrowitz et al. | 5/601 |
| 6,385,481 B2 | 5/2002 | Nose et al. | 600/415 |
| 6,557,195 B2 * | 5/2003 | Dinkler | 5/601 |
| 6,584,630 B1 * | 7/2003 | Dinkler | 5/622 |
| 6,640,364 B1 * | 11/2003 | Josephson et al. | 5/601 |
| 6,776,527 B1 * | 8/2004 | Tybinkowski et al. | 378/209 |
| 6,782,571 B1 * | 8/2004 | Josephson et al. | 5/601 |
| 6,813,788 B2 * | 11/2004 | Dinkler et al. | 5/622 |
| 6,973,689 B2 * | 12/2005 | Lenting et al. | 5/601 |
| 7,120,223 B2 * | 10/2006 | Nafstadius | 378/20 |
| 2004/0057557 A1 * | 3/2004 | Nafstadius | 378/209 |
| 2005/0034237 A1 * | 2/2005 | Lenting et al. | 5/600 |
| 2006/0167356 A1 * | 7/2006 | Everett et al. | 600/407 |

* cited by examiner

METHOD AND APPARATUS FOR AUTOMATIC SELF-ALIGNING DOCKING OF A COUCH WITH A MAGNETIC RESONANCE IMAGING SCANNER

CROSS REFERENCE TO RELATED APPLICATIONS

This application claims the benefit of U.S. provisional application Ser. No. 60/429,703 filed Nov. 27, 2002, which is incorporated herein by reference.

The following relates to the diagnostic imaging arts. It particularly relates to the docking and undocking of a couch or other movable subject support with a magnetic resonance imaging apparatus. The following relates more generally to rapid, safe, precise, and convenient transfer of a patient or other imaging subject into and out of various types of diagnostic imaging scanners such as magnetic resonance imaging scanners, computed tomography imaging scanners, nuclear cameras, positron emission tomography scanners, and the like.

In medical diagnostic imaging, an issue arises in the transfer of an imaging subject to and from the imaging apparatus. In many cases, the subject is disabled and unable to assist in the transfer process. In some instances it is important to preserve patient position.

Typically, the patient is placed on a wheeled patient couch or other movable subject support that is adapted to mechanically dock with the medical diagnostic magnetic resonance imaging scanner or other imaging apparatus. In one known approach, a locking mechanism that locks the couch to the imaging apparatus is triggered by operation of a brake pedal of the patient couch. Once connected, a conveyor belt of the imaging apparatus is linked with a patient supporting pallet or top of the patient couch, and the patient and pallet are transported into a magnet bore of the magnetic resonance imaging apparatus for imaging.

After the imaging session is complete, the patient and pallet are transported back and reconnected to the patient couch base. The operator disconnects the conveyor belt of the imaging apparatus from the patient couch. The brake pedal is released, which also unlocks the patient couch from the subject support, and the patient couch is wheeled away.

These patient transfer systems rely upon substantial operator input and coordination to dock and undock the patient successfully. The couch is manually aligned and moved into the docking position, and the locking mechanism of the couch with the imaging apparatus relies upon accuracy of such manual alignment. Moreover, there is a substantial possibility of operator error causing patient injury and/or damage to the couch and/or imaging apparatus if, for example, the couch is undocked prior to disconnection of the conveyor belt linkage.

The present invention contemplates an improved apparatus and method that overcomes the aforementioned limitations and others.

According to one aspect, a docking assembly is disclosed. The docking assembly is connected to a movable subject couch for docking the movable subject couch with an imaging apparatus. Couch alignment surfaces mate with corresponding imaging apparatus alignment surfaces of a connecting region of the imaging apparatus to define a docked position of the movable subject couch with respect to the imaging apparatus. A docking sensor detects the movable subject couch approaching the docked position. A latch mates with the connecting region of the imaging apparatus. An actuator cooperates with the latch to bias the movable subject couch into the docked position in response to the docking sensor detecting that the couch has approached the docking position.

According to another aspect, a method is provided for docking a movable subject support couch with an imaging apparatus. The movable subject support couch is moved toward the imaging apparatus. Responsive to the moving, a latch connected with the movable subject support couch mates with a connecting region of the imaging apparatus. The movable couch approaching a docked position with respect to the imaging apparatus is detected. Responsive to the detecting, the movable subject support couch is biased into the docked position using the mated latch as a first force anchor.

One advantage resides in reduced operator actions involved in subject docking and undocking.

Another advantage resides in a reduced likelihood of damage to the patient support and/or the imaging apparatus due to operator error in the docking or undocking.

Yet another advantage resides in improved docking and undocking reliability.

Still yet another advantage resides in self-alignment of the couch or other movable subject support with the imaging apparatus.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
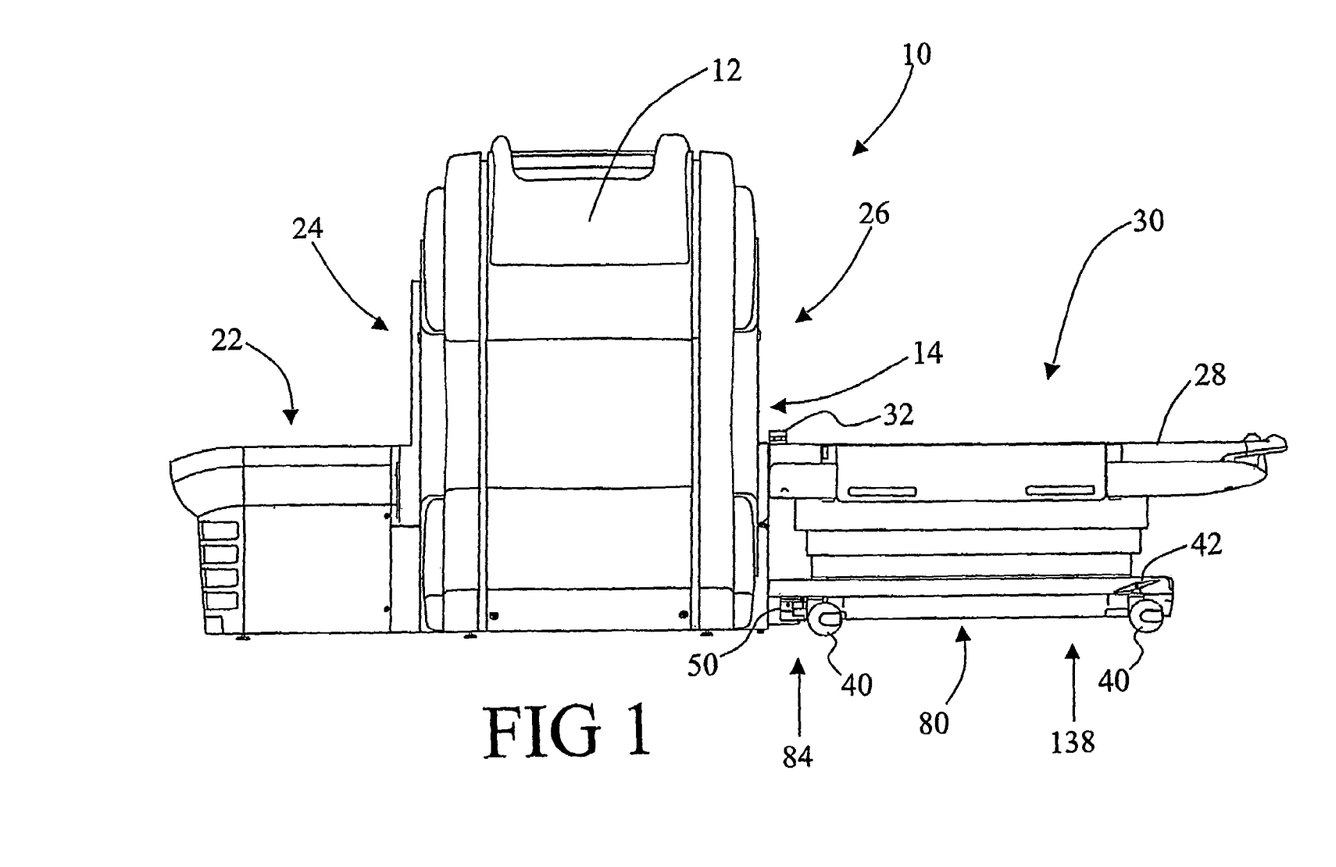
FIG. 1 shows a side view of a magnetic resonance imaging apparatus with a movable couch docked therewith.
Figure 2:
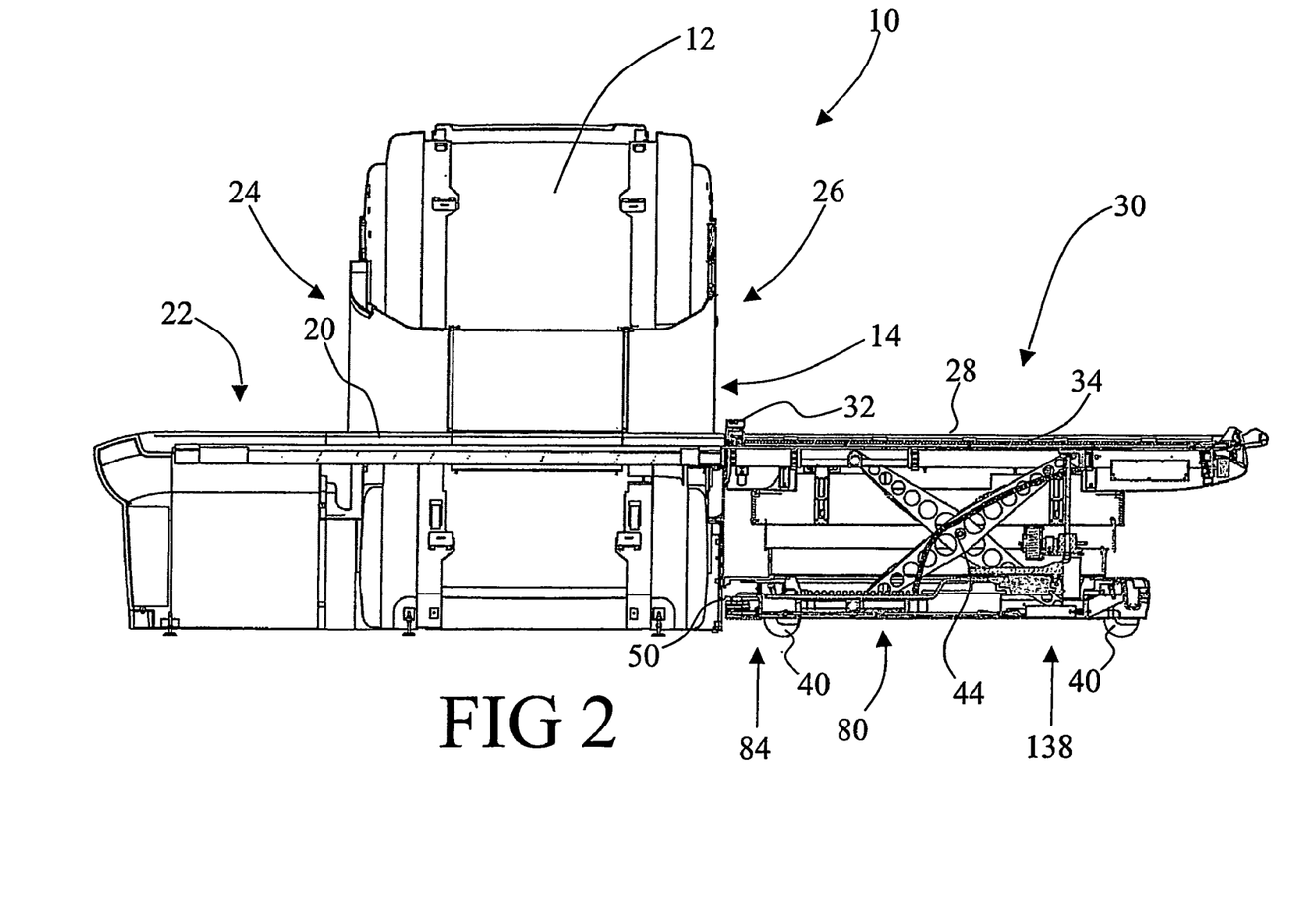
FIG. 2 shows a partial sectional view of the magnetic resonance imaging apparatus and docked movable couch of FIG. 1.

With reference to FIGS. 1 and 2, a magnetic resonance imaging apparatus 10 includes a housing 12 that encloses at least a main magnet which is preferably superconducting and cryoshrouded. The housing 12 defines a bore 14 inside which a subject is placed for imaging. Magnetic field gradient coils for spatially encoding the magnetic resonance signals are enclosed in the housing 12 or are arranged in the bore 14, as are one or more radio frequency coils and other optional components that are cooperatively used to generate, tailor, and detect magnetic resonance signals of the imaging subject.

A motorized belt or chain drive 20 passes through the bore 14. The belt 20 is linearly movable to position or move an imaging subject axially within the bore 14. The motorized belt 20 includes a portion 22 extending beyond a first side 24 of the housing 12 to enable the subject to be positioned with a portion extending outside the bore 14 on the first side 24.

On a second side 26 of the housing 12, the belt 20 cooperates with a movable subject support pallet or couch top 28 of a couch assembly 30 to define a continuous motorized subject transport that extends on both sides 24, 26 of the housing 12. Specifically, a coupling element 32 couples the belt 20 of the magnetic resonance imaging apparatus 10 with a subject support belt portion 34.

The movable couch 30 is detachably attached to the imaging apparatus 10. To enable the couch 30 to be moved when it is detached from the imaging scanner 10, the couch 30 includes wheels 40, rolling castors, or the like. One or more wheel brakes 42 are selectively operated to immobilize the couch 30. Preferably, the couch 30 also includes a height adjustment mechanism 44 for vertically aligning the coupling element 32 with the belt 20 of the imaging apparatus 10.

Figure 3:
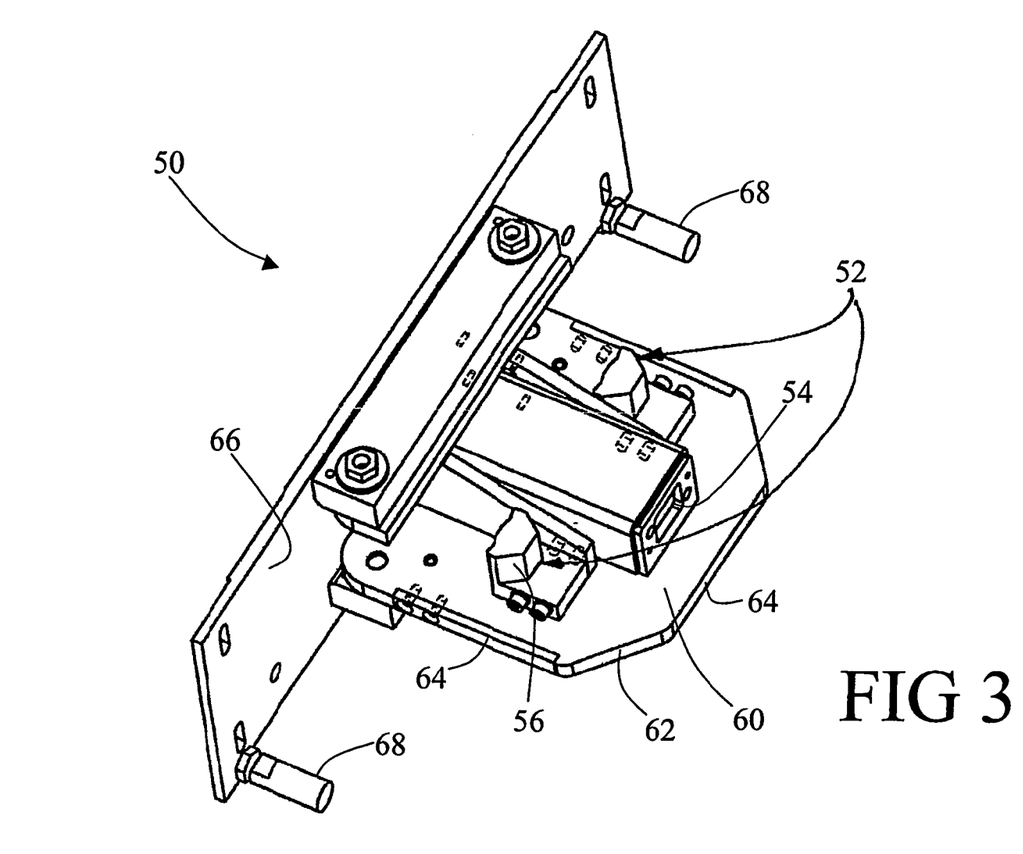
FIG. 3 shows a connecting region of the magnetic resonance imaging apparatus of FIGS. 1 and 2 that cooperates with a docking assembly of the movable couch in docking the movable couch with the magnetic resonance imaging apparatus.

With continuing reference to FIGS. 1 and 2, and with further reference to FIG. 3, the magnetic resonance imaging apparatus 10 includes a connecting region 50 that provides alignment and force anchoring for aligning and securing the movable couch 30 with the imaging apparatus 10. In the illustrated embodiment, the connecting region 50 includes two latching blocks 52 on opposite sides of an electronic connector 54. The electrical connector 54 provides for optional electrical communication between the imaging apparatus 10 and the movable couch 30, for example to communicate sensor readings therebetween or to deliver electrical power and/or control signals from the imaging apparatus 10 to the movable couch 30. Each latching block 52 includes a camming surface 56 for camming a latch or other mating component of the subject support 30 onto the latching block 52.

Placement of the two latching blocks 52 on opposite sides of the electrical connector 54 advantageously arranges the force anchoring symmetrically with respect to the imaging apparatus 10. However, if the optional electrical connector 54 is omitted, a single centrally positioned latching block can be employed. Of course, more than two latching blocks can also be included to provide additional force anchoring points.

The connecting region 50 also includes a tongue 60 that extends away from the imaging apparatus 10. The tongue 60 includes camming surfaces 62 for facilitating lateral alignment of the couch 30 with the imaging apparatus 10 during docking. The tongue 60 further includes alignment surfaces 64 disposed on the tongue edges that cooperate with corresponding surfaces of the docking assembly to define a docked position with the movable couch 30 in line with the bore 14. A mounting plate 66 secures the connecting region 50 with the second side 26 of the imaging apparatus 10. Alternatively, the connecting region 50 can be integrated with the housing 12. Preferably, the connecting region 50 includes stops 68 that limit movement of the couch 30 toward the imaging apparatus 10 and limit skewing to assure that the couch 30 is in line with the bore 14.

With continuing reference to FIGS. 1-3 and with further reference to FIGS. 4-8, a lower portion 70 of the movable couch 30 includes a docking assembly that cooperates with the connecting region 50 of the magnetic resonance imaging apparatus 10 to detachably secure the movable couch 30 with the magnetic resonance imaging apparatus 10. The docking assembly includes alignment surfaces 72 with rollers or bearings 74 that cooperate with the alignment surfaces 64 of the tongue 60 of the connecting region 50 of the imaging apparatus 10 to define the docked position of the movable couch 30 respective to the imaging apparatus 10. The rollers or bearings preferably also serve as camming surfaces that cooperate with the camming surfaces 62 of the tongue 60 of the connecting region 50 to urge the movable couch 30 laterally toward the docked position as the couch 30 approaches the imaging apparatus 10.

Figure 4:
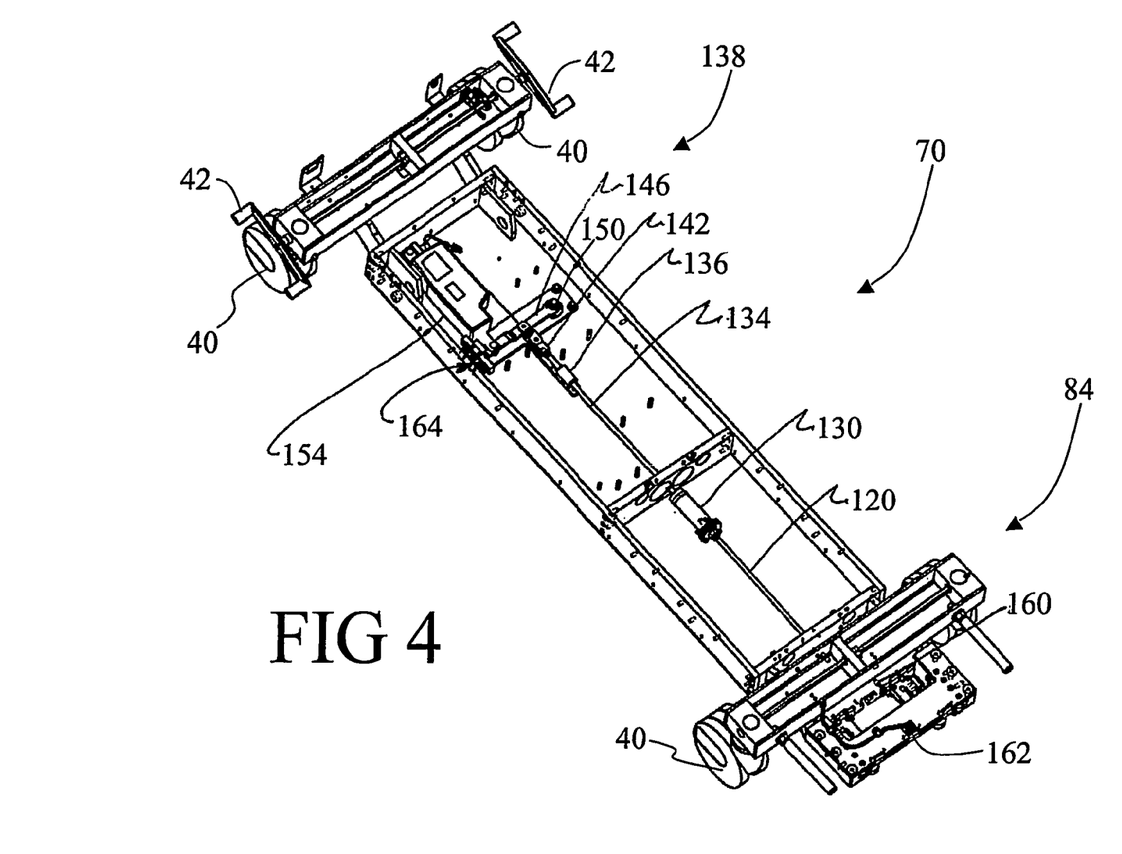
FIG. 4 shows an overhead perspective view of a lower portion of the movable couch including components of the docking assembly.
Figure 5:
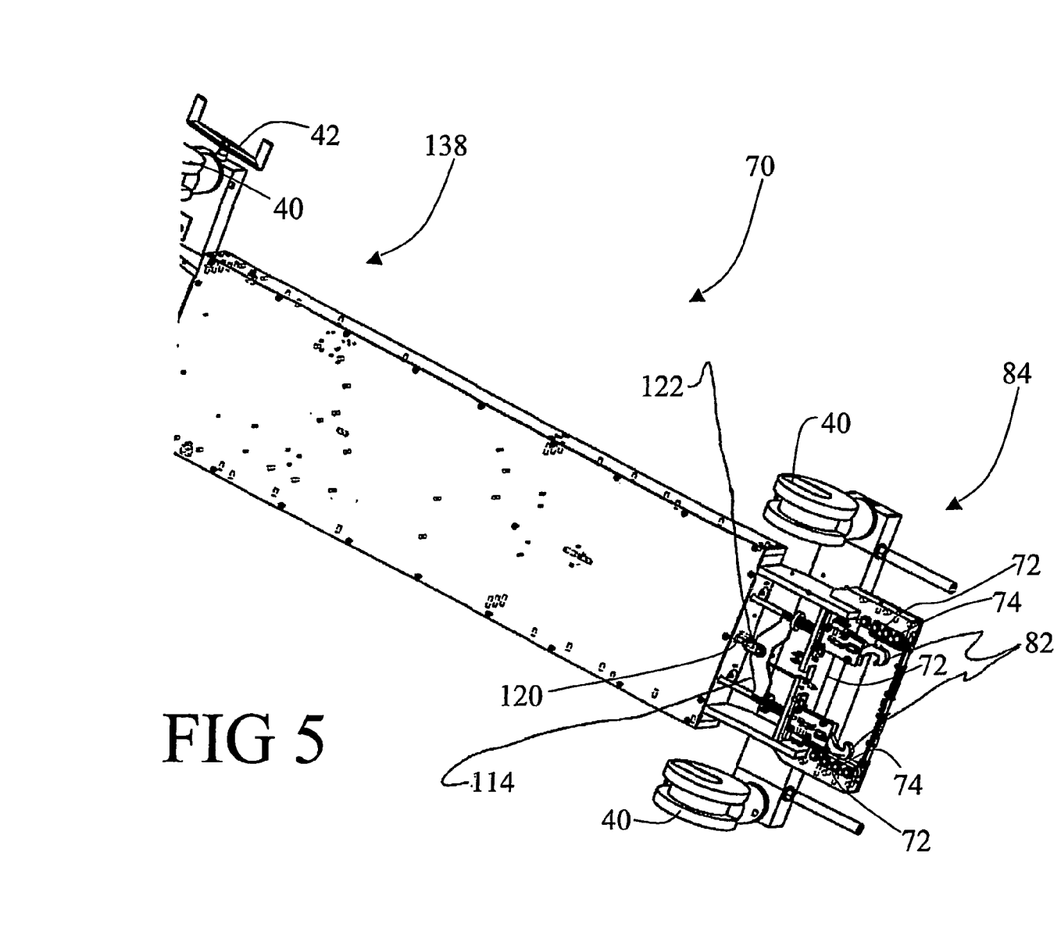
FIG. 5 shows a perspective view from below of the lower portion of the movable couch shown in FIG. 4.

The docking assembly further includes latches 82 disposed at a forward end 84 of the couch 30 that detachably latch with the two latching blocks 52. In the illustrated embodiment, there are two latches 82 corresponding to the two latch blocks 52. An alternative embodiment with a single centrally located latch block will typically include a single corresponding latch, rather than the two latches shown.

In the illustrated embodiment, each latch 82 includes a hook 86 that is spring-biased to a closed position by a leaf spring 88. (Best seen in FIGS. 7 and 8). The leaf spring 88 is secured to a guide block 90 at one end, and is preferably secured to the hook 86 by a fastener 92. The guide block is secured to the lower portion 70 of the movable couch 30. (Best seen in FIG. 5). The hook 86 of each latch 82 pivots about a clevis pin 94 that in turn is connected with a clevis yoke 96 to allow the hook 86 to open in opposition to the biasing force produced by the leaf spring 88.

Figure 7:
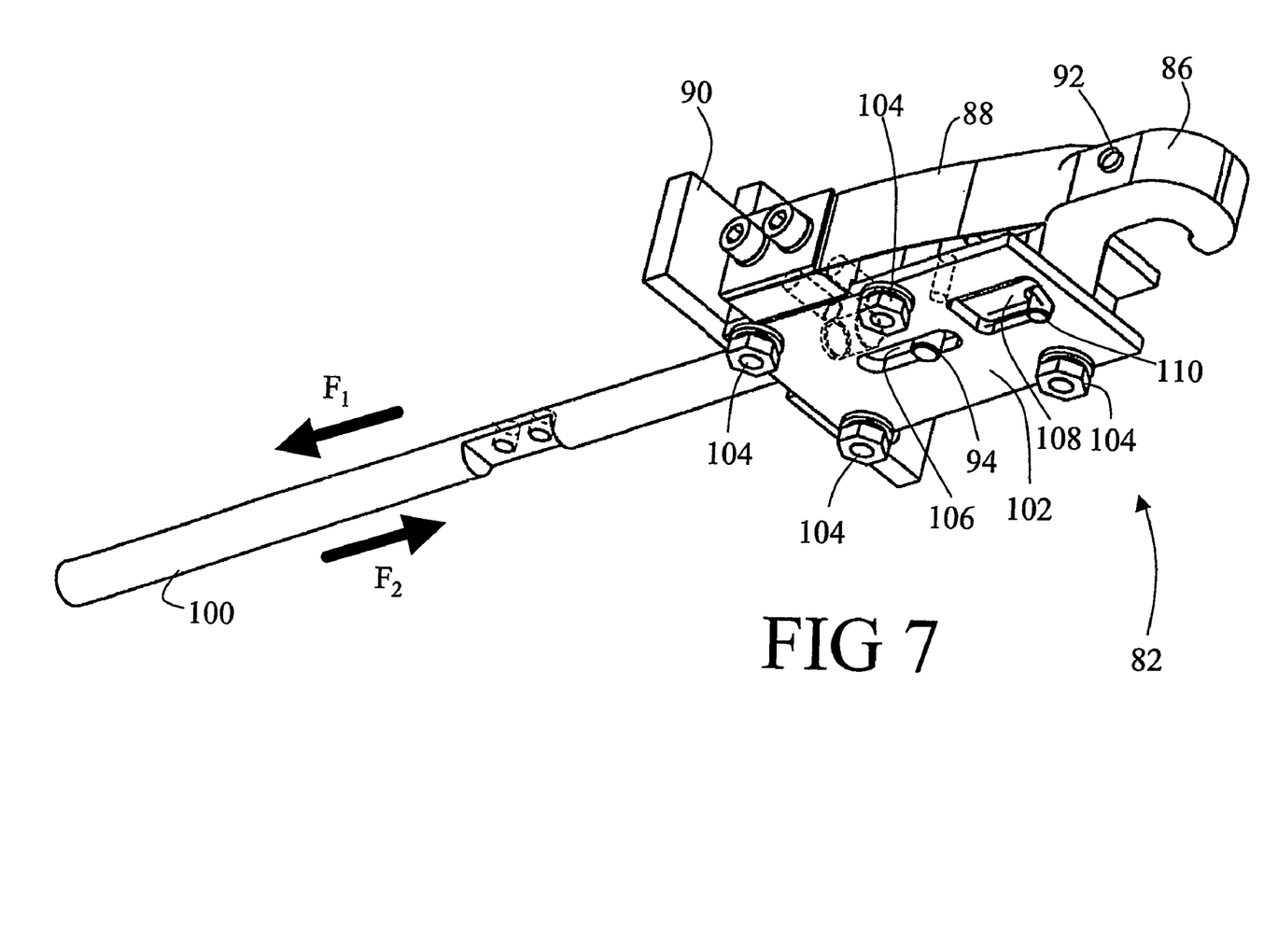
FIG. 7 shows a perspective view of one of the latches including a guide plate.
Figure 8:
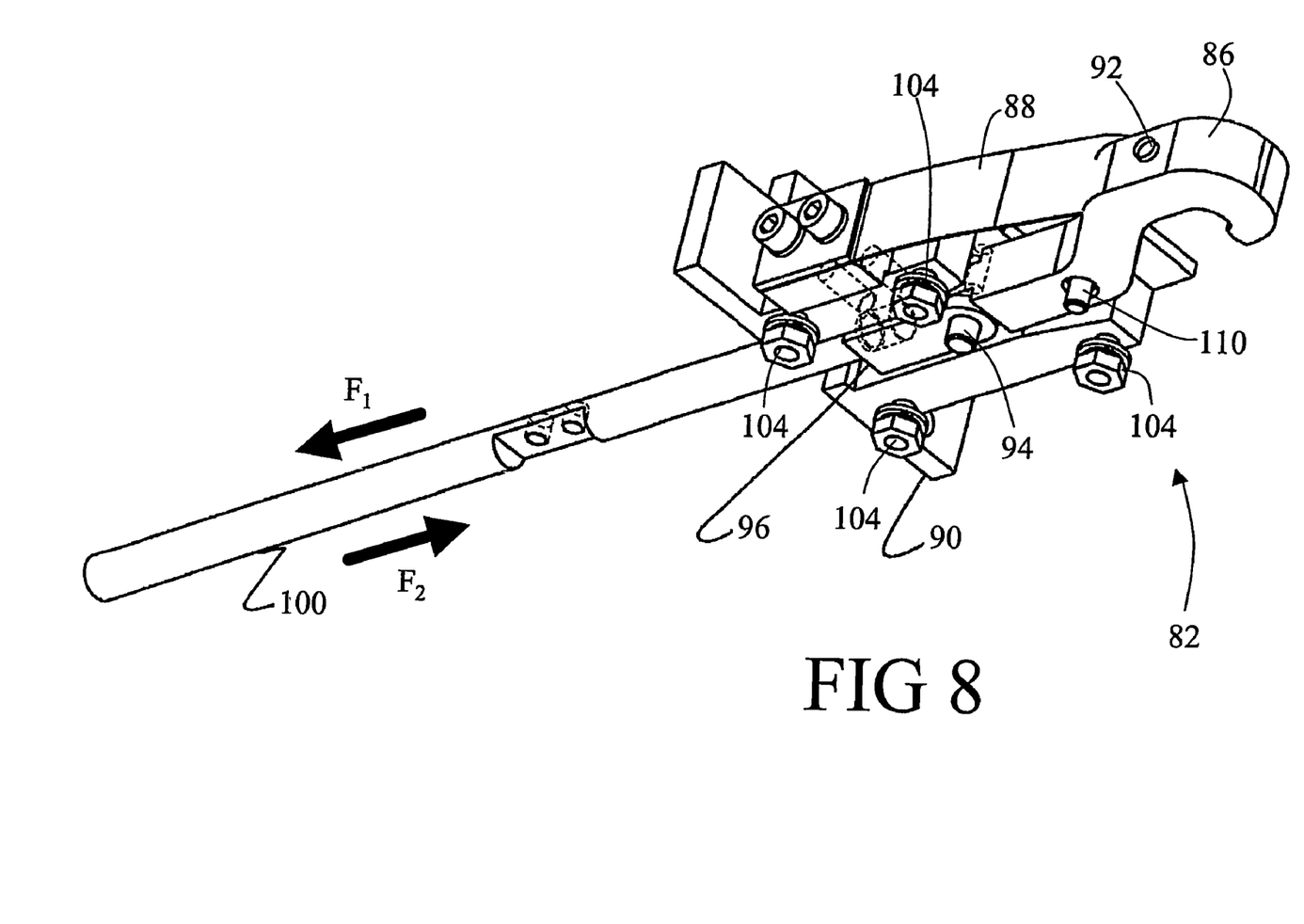
FIG. 8 shows a perspective view of the latch of FIG. 7 with the guide plate removed.

The clevis yoke 96 is fastened to a guide rod 100 that slidably passes through the guide block 90. A guide plate 102 is secured to the guide block 90 via fasteners 104. (Note that the guide plate 102 is shown in FIG. 7, and is removed in FIG. 8 to show underlying components). The guide plate 102 includes a first narrow slot 106 that cams the clevis pin 94, and a second wider slot 108 that cooperates with a camming pin 110 to guide opening and closing of the latch 82.

Figure 6:
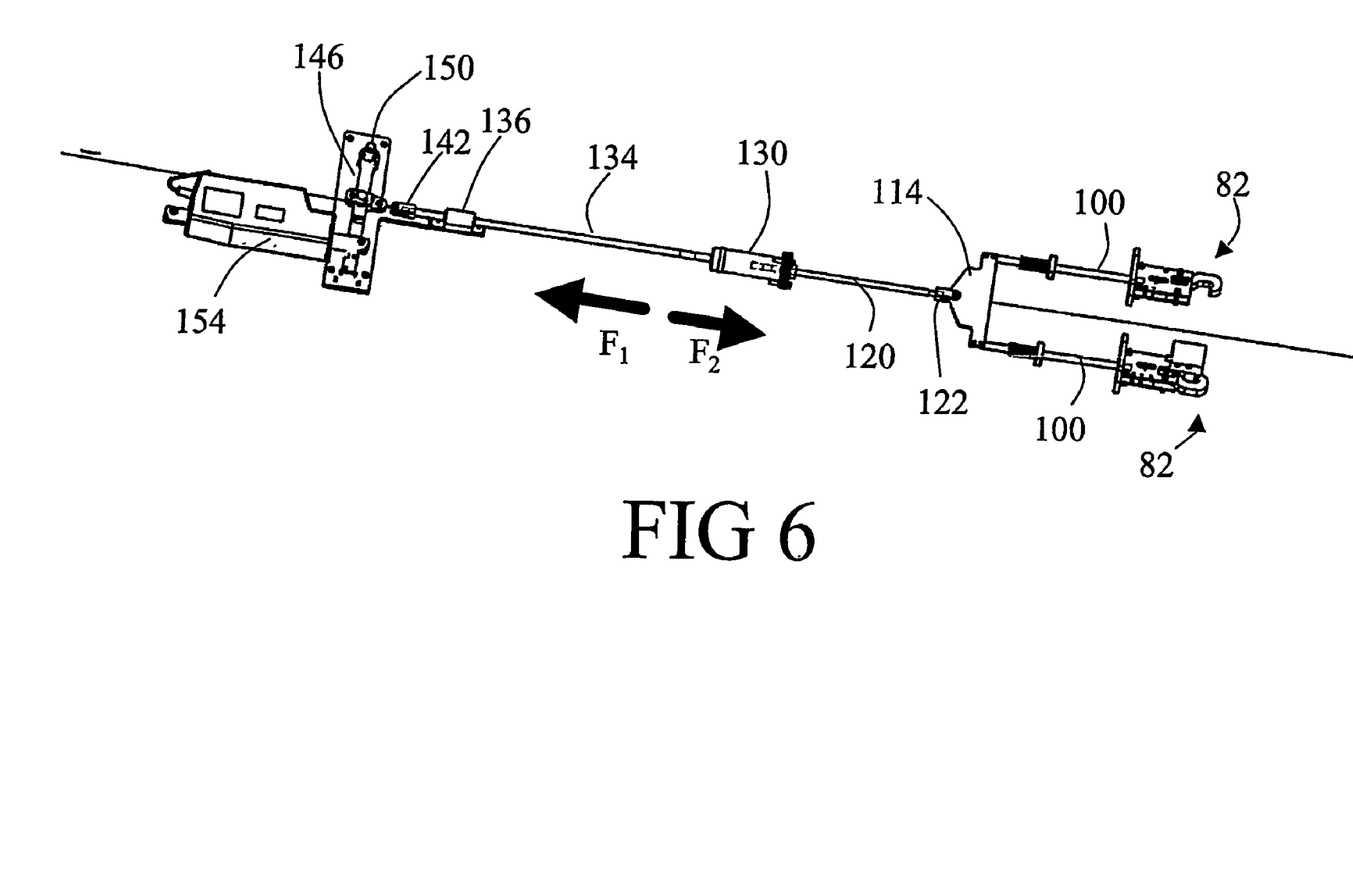
FIG. 6 shows a perspective view of a portion of the docking assembly including an actuator, connecting rods, mechanical fittings, a spring cartridge assembly, a divider plate, and latches.

The guide rod 100 of each of the two latches 82 connects with a divider plate 114 that distributes an actuator force between the two latches 82. As shown in FIG. 6, ends of the guide rods 100 can connect to the divider plate 114. Alternatively, as shown in FIG. 5, each guide rod 100 can connect at an intermediate point such that the guide rod 100 also passes through a caster weldment of the couch 30 to assist in guiding and dividing actuator force between the two guide rods 100.

The divider plate 114 in turn connects with a front connecting rod 120 via a pivotable clevis block 122 that is pinned to the divider plate 114. The front connecting rod 120 includes a threaded opposite end that threads into a spring cartridge assembly 130. A rear connecting rod 134 has a threaded end that threads into the spring cartridge assembly 130 and extends away from the forward end 84 of the movable couch 30 through a guide block 136 toward a rear end 138 of the couch 30. The rear connecting rod 134 connects with another clevis block 142 that is pinned to a pivotable drive link 146. The pivotable drive link pivots about a pivot 150 fixed to the weldment of the movable couch 30.

An actuator motor 154 delivers the actuator force to the pivotable drive link 146 at an end of the drive link 146 opposite the pivot 150. A second class lever is thus defined in which the load-coupling clevis block 142 is arranged between the applied force produced by the actuator motor 154 and a lever fulcrum defined by the pivot 150. The hooks 86 are cammed apart during movement of the couch 30 and are biased by the leaf springs 88 onto the blocks 52. To undock, the actuator motor 154 applies a force to the linkage which moves the hooks 86 apart, away from the blocks 52. In one suitable embodiment, the actuator motor 154 is a battery-driven 24 volt self-locking linear actuator motor.

With continuing reference to FIGS. 1-8, the docking assembly further includes various sensors for sensing various stages of docking and undocking. In the illustrated embodiment, these sensors include a start dock sensor 160 suitably embodied as a plunger switch that is activated or turned on (that is, plunger depressed) when the movable couch 30 approaches the docked position such that the plunger contacts a surface of the connecting region 50 of the imaging apparatus 10. A flipper switch 162 similarly detects when the movable couch 30 is secured in the docked position, and when the couch 30 is substantially free from the docked position during undocking. A brake switch detects whether the wheel brake 42 is on or off.

Optical switch sensors 164 indicate a state of the drive link 146. In a preferred embodiment, three drive link optical switch sensors 164 indicate whether the drive link 146 is in: (i) an undocked position in which the drive link 146 is pivoted toward the rear end 138 of the couch 30; (ii) a docked position in which the drive link 146 is pivoted toward the front end 84 of the couch 30; or (iii) a ready-to-dock position in which the drive link 146 is pivoted into an intermediate position between the front end 84 and the rear end 138 of the couch 30.

Figure 9:
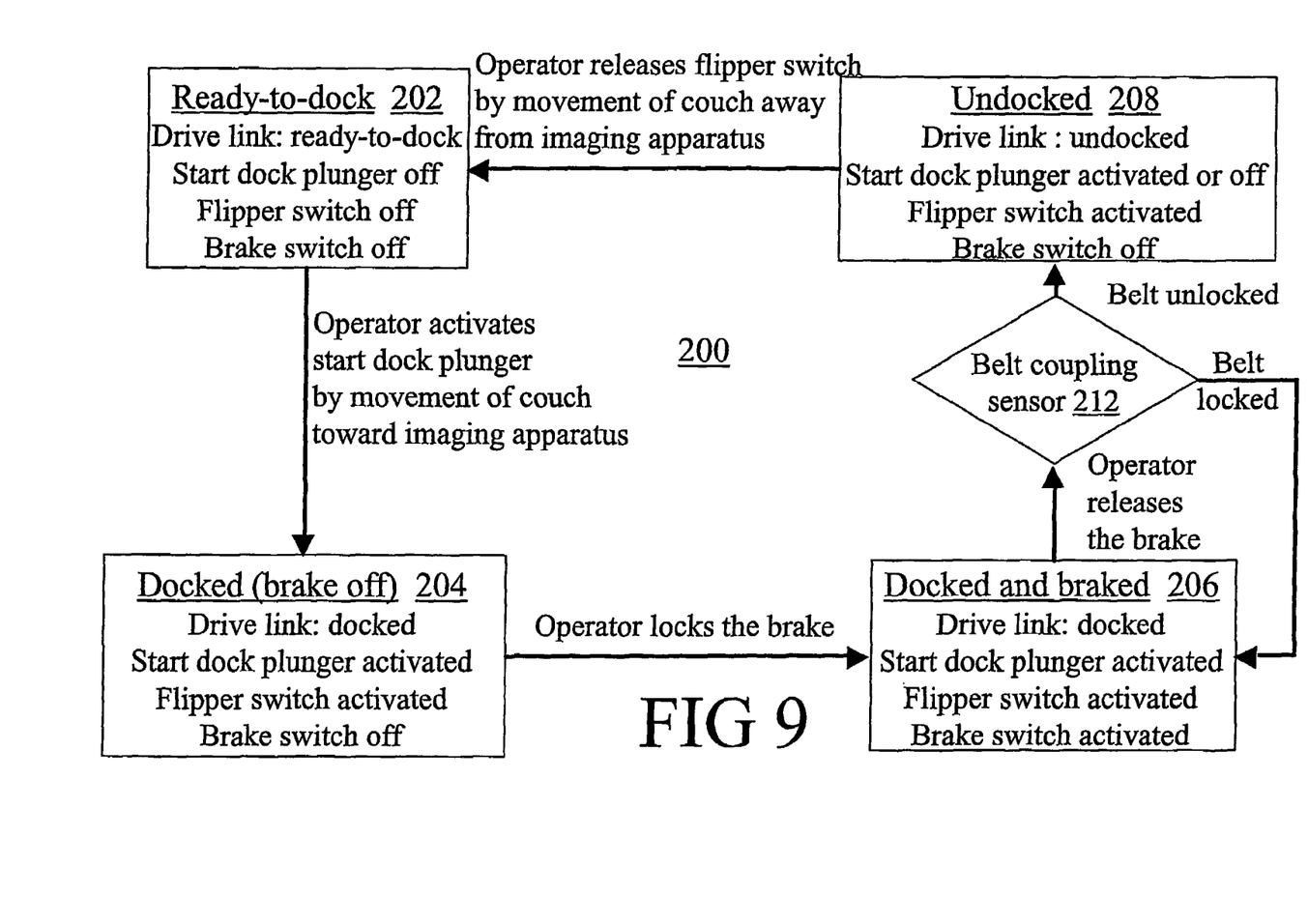
FIG. 9 diagrammatically shows a state diagram of a state machine controller that controls the docking and undocking processes.

With continuing reference to FIGS. 1-8 and with further reference to FIG. 9, the docking assembly preferably includes a state machine controller whose state diagram 200 is schematically represented in FIG. 9. The state machine controller is preferably embodied by a microprocessor or microcontroller disposed on the movable couch 30 that monitors the sensors and implements the state diagram 200.

The exemplary state diagram 200 includes four states. In a ready-to-dock state 202, the optical sensor 164 indicates the ready-to-dock position of the drive link 146, and the start dock plunger sensor 160, the flipper switch 162, and the brake switch are off. In a docked state 204, the optical sensor 164 indicates the docked position of the drive link 146, the start dock plunger sensor 160 and the flipper switch 162 are both activated, but the brake switch is off. A docked-and-braked state 206 is similar to the docked state 204 except that the brake sensor indicates the brake is on. In an undocked state 208, the optical sensor 164 indicates the undocked position of the drive link 146, the flipper switch 162 is activated, and the brake switch is off.

The exemplary state diagram 200 suitably implements a docking process that starts at the ready-to-dock state 202. An operator rolls the movable couch 30 on its wheels 40 toward the connecting region 50 of the imaging apparatus 10. During this movement, the camming surfaces 62 of the connecting region 50 of the imaging apparatus 10 contact and cam with the rollers 74 or other camming surfaces of the docking assembly to urge the couch 30 toward the docked position. Similarly, the hooks 86 of the latches 82 contact the camming surfaces 56 of the latch blocks 52 of the connecting region 50 and cam open against the biasing force exerted by the leaf springs 88. As continued movement of the couch 30 moves the hooks 86 past the camming surfaces 56, the hooks 86 close onto the latching blocks 52 due to the biasing of the leaf springs 88.

Continued movement of the couch 30 toward the docked position causes the start dock plunger 160 to be pushed in, triggering a transition from the ready-to-dock state 202 to the docked state 204. The actuator motor 154 is driven to pivot the drive link 146 from the ready-to-dock position to the docked position. This movement produces an actuator force $F_1$ pulling on the rear connecting rod 134. Initially, the actuator force $F_1$ transfers through the rear connecting rod 134, the spring cartridge assembly 130, and the front connecting rod 120, and is distributed by the divider plate 114 and the guide rods 100 to the two latches 82. Thus, the actuator force $F_1$ is a tensile force acting between a rear force anchor point corresponding to the motor 154 and the drive link 146, and a front force anchor point defined by the connection of the latches 82 onto the latch blocks 52.

The tensile actuator force $F_1$ draws the movable couch 30 into the docked position. Once docked, the motor 154 continues to operate to transfer and store a predetermined amount of mechanical energy in the spring cartridge assembly 130. In a preferred embodiment, the spring cartridge assembly 130 is loaded to about 55 kg. Once the spring cartridge assembly 130 is loaded to the desired value, the motor 154 ceases operation.

Thus, when the motor 154 ceases operation the movable couch 30 remains biased and secured in the docked position by the loaded spring cartridge assembly 130. The docked state 204 is indicated by the optical sensors 164. To ensure the movable couch 30 is secured, the user is preferably prompted by a display or other indicator to engage the brakes. The operator engages the wheel brake 42. Engaging the wheel brake 42 activates the brake switch and places the docking assembly into the docked-and-braked state 206.

Once docked and braked, the operator connects and locks the belt coupling element 32 to the belt 20 of the imaging apparatus 10. Once the connection is sensed, a lock which locks the subject pallet or couch top 28 to the couch 30 is released. The belt 20 transfers the subject pallet 28 into the magnet bore 14 of the imaging apparatus 10. The operator causes the imaging apparatus 10 to perform selected magnetic resonance imaging operations on the subject, and transfers the subject back to the movable couch 30 via the linked belts 20, 34.

Once the pallet 28 is locked to the couch 30, the operator can initiate undocking by decoupling the coupling element 32 and releasing the wheel brake 42. Preferably, transition from the docked-and-braked state 206 to the undocked state 208 is initiated by release of the wheel brake 42. However, the transition preferably also is contingent upon a tabletop sensor 212 (operatively represented in FIG. 9) indicating that the conveyor belt coupling element 32 is unlocked and the pallet 28 is locked to the couch 30. This reduces the likelihood of damage to the conveyor belts 20, 34 or the coupling element 32.

To undock, the motor 154 operates in a reverse direction to pivot the drive link 146 from the rearward docked position to the forward undocked position. This exerts an actuator force $F_2$ on the rear connecting rod 134 directed toward the front end 84. Initially, the actuator force $F_2$ transfers through the rear connecting rod 134 to the spring cartridge assembly 130 to unload the spring cartridge assembly 130. That is, in the exemplary embodiment the 55 kg stored in the spring cartridge assembly 130 is unloaded.

Once the spring cartridge assembly 130 is unloaded, the actuator force $F_2$ transfers through the rear connecting rod 134, the spring cartridge assembly 130, and the front connecting rod 120, and is distributed by the divider plate 114 and the guide rods 100 to the two latches 82. The actuator force $F_2$ drives each hook 86 forward. During this forward motion, the clevis pin 94 cams in the first narrow slot 106 and the camming pin 110 cams in the second wider slot 108 of the guide block 90 to guide the hook 86 into an open position against the biasing force of the leaf spring 88.

When the drive link 146 reaches the undocked position as indicated by the drive link optical switch sensors 164, the latches 82 are retained in the open position. The operator can then move the couch 30 away from the imaging apparatus 10. The movement draws the opened latches 82 past the latch blocks 52 of the connection region 50 of the imaging apparatus 10. Continued movement causes the flipper switch 162 to deactivate, indicating that the latches 82 are clear of the latching blocks 52.

Deactivation of the flipper switch 162 initiates a transition from the undocked state 208 to the ready-to-dock state 202. To make this transition, the motor 154 moves the drive link 146 from the undocked position to the intermediate ready-to-dock position. The movement transfers through the rear connecting rod 134, the spring cartridge assembly 130, and the front connecting rod 120, and is distributed by the divider plate 114 and the guide rods 100 to the two latches 82. The actuator force $F_2$ holding the hooks 86 open is released so that the closing bias provided by the leaf springs 88 causes the hooks 86 to be biased into the closed position.

Docking and undocking of the movable couch 30 with the exemplary magnetic resonance imaging apparatus 10 is described herein. However, those skilled in the art can readily adapt the described docking assembly to perform docking and undocking of a patient couch or other movable imaging subject support with other types of magnetic resonance imaging scanners, or with a computed tomography imaging apparatus, a nuclear camera, a positron emission tomography imaging apparatus, a radiotherapy apparatus, or the like.

Having thus described the preferred embodiments, the invention is now claimed to be:

1. A docking assembly for docking a movable subject couch with an imaging apparatus, the docking assembly including:
    couch alignment surfaces that mate with corresponding imaging apparatus alignment surfaces of a connecting region of the imaging apparatus to define a docked position of the movable subject couch with respect to the imaging apparatus;
    a docking sensor that detects the movable subject couch approaching the docked position;
    a latch that mates with the connecting region of the imaging apparatus; and
    an actuator that cooperates with the latch to bias the movable subject couch into the docked position in response to the docking sensor detecting that the couch has approached the docking position, the actuator including an electric motor and a mechanical energy storage element interposed between the motor and the latch, the mechanical energy storage element cooperating with the latch to bias the movable subject couch into the docked position when the motor is not delivering mechanical energy.

2. The docking assembly as set forth in claim 1, further including:
    rolling elements arranged between the couch alignment surfaces and the corresponding imaging apparatus alignment surfaces of the connecting region of the imaging apparatus.

3. The docking assembly as set forth in claim 1, wherein the docking assembly further includes:
    couch camming surfaces that cooperate with camming surfaces of the connecting region of the imaging apparatus to cam the movable subject couch laterally toward alignment with the docked position as the movable subject couch approaches the imaging apparatus.

4. The docking assembly as set forth in claim 1, wherein the latch includes:
    a biasing spring; and
    a hook that is biased by the biasing spring toward a closed position, the hook being cammed opened in opposition to the biasing spring by a camming surface of a latch block as the movable subject couch approaches the docked position, the biasing spring biasing the hook to close onto the latch block as the hook moves past the camming surface and ceases contact therewith.

5. The docking assembly as set forth in claim 1, wherein the mechanical energy storage element includes a spring interposed between the motor and the latch.

6. The docking assembly as set forth in claim 5, wherein the actuator further includes:
    a drive shaft arranged between the motor and the latch, the motor driving the drive shaft in a first direction to secure the latch onto the latch block of the connecting region of the imaging apparatus, the spring storing energy received from the motor during the driving in the first direction, the stored energy continuing to bias the latch on the latch block after the driving in the first direction ceases.

7. The docking assembly as set forth in claim 6, further including:
    an undock camming surface that communicates with the latch to cam the latch open when the motor drives the drive shaft in a second direction opposite the first direction.

8. A magnetic resonance imaging apparatus including:
    a housing that houses at least a main magnet and magnetic field gradient coils and defines a bore;
    a movable subject couch; and
    the docking assembly as set forth in claim 1 for docking the movable subject couch with the housing.

9. The magnetic resonance imaging apparatus as set forth in claim 8, wherein the connecting region further includes:
    a tongue extending from the housing, the tongue defining the imaging apparatus alignment surfaces; and
    a latch block disposed on the tongue, the latch selectively latching onto the latch block.

10. A docking assembly for docking a movable subject couch with an imaging apparatus, the docking assembly including:
    couch alignment surfaces that mate with corresponding imaging apparatus alignment surfaces of a connecting region of the imaging apparatus to define a docked position of the movable subject couch with respect to the imaging apparatus;
    a docking sensor that detects the movable subject couch approaching the docked position;
    a latch that mates with the connecting region of the imaging apparatus;
    an actuator that cooperates with the latch to bias the movable subject couch into the docked position in response to the docking sensor detecting that the couch approached the docking position; and
    an electronic controller communicating with the actuator and the docking sensor, the electronic controller operating the actuator to cooperate with the latch to bias the movable subject couch into the docked position in response to the docking sensor detecting the movable subject couch approaching the docked position.

11. The docking assembly as set forth in claim 10, wherein the electronic controller monitors a state of the docking assembly, the docking assembly being in one of a plurality of states including:
- a ready to dock state in which the latch is biased into a closed position and the electronic controller is waiting for the docking sensor to detect the movable subject couch approaching the docked position;
- a docked state in which the latch is biased into the closed position and secured to the connecting region by the actuator; and
- an undocking state in which the latch is biased into an open position by the actuator.

12. The docking assembly as set forth in claim 11, further including;
- a tabletop lock sensor that indicates a locked condition of a subject transfer pallet of the movable subject couch, the electronic controller monitoring the tabletop lock sensor and prohibiting a docking assembly state transfer from the docked state to the undocking state when the tabletop lock sensor indicates an unlocked condition.

13. The docking assembly as set forth in claim 11, further including:
- an actuator sensor that indicates a position of the actuator, the electronic controller identifying the docking assembly state based on at least the docking sensor and the actuator sensor.

14. A couch including:
- a wheeled subject support; and
- a docking assembly set forth in claim 10 for docking the wheeled subject support with a diagnostic imaging apparatus.

15. The couch as set forth in claim 14, wherein the actuator includes:
- a motor disposed on the movable subject support that selectively drives the latch to mate with the connecting region of the imaging apparatus.

16. The couch as set forth in claim 15, wherein the actuator further includes:
- a spring disposed between the motor and the latch, the spring being mechanically loaded when the motor drives the latch to mate with the connecting region, the loaded spring biasing the latch into the mated position when the motor ceases the driving.

17. The docking assembly as set forth in claim 10, further including:
- rolling elements arranged between the couch alignment surfaces and the corresponding imaging apparatus alignment surfaces of the connecting region of the imaging apparatus.

18. The docking assembly as set forth in claim 10, wherein the docking assembly further includes:
- couch camming surfaces that cooperate with camming surfaces of the connecting region of the imaging apparatus to cam the movable subject couch laterally toward alignment with the docked position as the movable subject couch approaches the imaging apparatus.

19. The docking assembly as set forth in claim 10, wherein the latch includes:
- a biasing spring; and
- a hook that is biased by the biasing spring toward a closed position, the hook being cammed opened in opposition to the biasing spring by a camming surface of a latch block as the movable subject couch approaches the docked position, the biasing spring biasing the hook to close onto the latch block as the hook moves past the camming surface and ceases contact therewith.

20. A magnetic resonance imaging apparatus including:
- a housing that houses at least a main magnet and magnetic field gradient coils and defines a bore;
- a movable subject couch; and
- the docking assembly as set forth in claim 10 for docking the movable subject couch with the housing.

21. A method for docking a movable subject support couch with an imaging apparatus, the method including:
- moving the movable subject support couch toward the imaging apparatus;
- responsive to the moving, mating a latch connected with the movable subject support couch with a connecting region of the imaging apparatus;
- detecting the movable couch approaching a docked position with respect to the imaging apparatus; and
- responsive to the detecting, electromechanically biasing the movable subject support couch into the docked position using the mated latch as a first force anchor.

22. The method as set forth in claim 21, further including:
- locking a couch brake after the movable couch is biased into the docked position; and
- responsive to an unlocking of the couch brake, removing the biasing of the movable couch into the docked position and unmating the latch from the connecting region of the imaging apparatus.

23. The method as set forth in claim 21, wherein the biasing of the movable subject support couch into the docked position includes:
- relatively drawing a second force anchor disposed on the movable couch toward the first force anchor defined by the mated latch.

\* \* \* \* \*